US005263074A

United States Patent [19]

Sakamoto

[11] Patent Number: 5,263,074

[45] Date of Patent: Nov. 16, 1993

[54] SPOOL DISTORTION CORRECTION METHOD FOR AN X-RAY RADIOGRAPH DIAGNOSIS DEVICE

[75] Inventor: Hidenobu Sakamoto, Amagasaki, Japan

[73] Assignee: Mitsubishi Denki Kabushiki Kaisha, Tokyo, Japan

[21] Appl. No.: 869,506

[22] Filed: Apr. 16, 1992

[30] Foreign Application Priority Data

Apr. 17, 1991 [JP] Japan ................................ 3-084956

[51] Int. Cl.[5] .......................... H05G 1/64; A61B 6/00

[52] U.S. Cl. ........................................ 378/99; 378/62; 358/111

[58] Field of Search ..................... 378/99, 98, 62, 204, 378/205, 207, 162, 163, 164; 358/111

[56] References Cited

U.S. PATENT DOCUMENTS 4,048,507 9/1977 de Gastor ........................... 378/164

FOREIGN PATENT DOCUMENTS 2-10636 1/1990 Japan .

OTHER PUBLICATIONS

"Implementing an Automatic Control System for Dynamic Radiography", Heimer et al, *Medical & Biological Engineering & Computing*, vol. 15, No. 2, Mar. 1977, pp. 168–178.

*Primary Examiner*—David P. Porta

*Attorney, Agent, or Firm*—Rothwell, Figg, Ernst & Kurz

[57] ABSTRACT

In accordance with the distortion correction method for an X-ray radiograph diagnosis device, the distortion center of the X-ray image is determined by use of a plate-shaped object having a circular marker M and a marker center $M_0$. On the basis of the positions of the sample points $M_1$ through $M_4$ upon the circular marker M, the distortion center is inferred. Further, a grid marker pattern is used to determine the magnitudes of pincushion distortion at respective distances from the distortion center. The correction coefficients for correcting the spool distortion at respective distances from the distortion center are determined on the basis of the relationship between the physical and displayed distances from the marker center $M_0$ to the sample points.

13 Claims, 6 Drawing Sheets

SPOOL DISTORTION CORRECTION METHOD FOR AN X-RAY RADIOGRAPH DIAGNOSIS DEVICE

BACKGROUND OF THE INVENTION

This invention relates to correction methods for correcting distortions, especially spool distortions, of a screen image of the X-ray radiograph diagnosis devices by which a medical diagnosis can be effected with high accuracy on the basis of the radiographs of high quality.

Generally, in the case of the medical diagnosis based on an X-ray radiograph imaged displayed on screen, an object is positioned between an X-ray tube and an X-ray image intensifier. An X-ray transmitted through the object is detected and converted into a digital signal. The diagnosis is effected on the basis of the digital signal. However, the image obtained from the X-ray image intensifier generally contains a geometric distortion peculiar to an electron lens system. The distortion is referred to as the spool distortion since a square is distorted into the form of a spool. Since the distortion impairs the geometric accuracy of the X-ray image, various correction methods have hitherto been proposed.

For example, FIG. 5 is a diagram showing a structure of a conventional X-ray radiograph diagnosis device, which is disclosed in Japanese Laid-Open Patent (Kokai) No. 2-10636. In FIG. 5, the X-ray R is exposed from an X-ray tube 1 which is vertically translatable as indicated by the double-headed arrow. An X-ray image intensifier 2 disposed coaxially with the X-ray tube 1 opposes the X-ray tube 1 to receive the transmitted X-ray R. An object 3 is positioned between the X-ray tube 1 and the X-ray image intensifier 2. An image processor 4 coupled to the X-ray image intensifier 2 digitizes a signal obtained by the transmitted X-ray R. A display device 5 displays the digitized screen image obtained by the image processor 4.

FIG. 6 is an axial sectional view showing the details of the X-ray image intensifier of FIG. 5. The X-ray tube focus 10 corresponds to the radiation source of the X-ray tube 1. A vacuum tube 20 accomodates the following: a photoelectric cathode 21 which generates photoelectrons E upon receiving the X-ray R transmitted through the object 3. As shown in FIG. 6 (the object 3 may, for example, be a plate-shaped object instead of a human body when a test, for example, is performed); a plurality of grid electrodes 22 converges photoelectrons E to the cross-over point P; a front stage anode 23 and a back stage anode 24 together constitute an electron lens system for photoelectrons E passing the cross-over point P; an intermediate electrode for correction 25 interposed between the front stage anode 23 and the back stage anode 24; and a fluorescent film 26 having an output surface 26*a* which emits light in accordance with a strength of receiving the photoelectrons E. The trajectory distance between the X-ray from the X-ray focus 10 and the photoelectric cathode 21 is represented by FID.

FIG. 7 is a diagram showing the magnitude of the spool distortion (plotted along the ordinate) in relation to distance from a distortion center (plotted along the abscissa) for various values of X-ray trajectory distance FID. The abscissa represents the distance from the distortion center of the spool distortion, where an outer radius is plotted at 100 percent. The ordinate represents an integral of the geometric distortion corresponding to the magnitude of the spool distortion. The respective curves correspond to the cases where the X-ray trajectory distance FID from the X-ray focus 10 to the photoelectric cathode 21 varies from 1000 mm to 700 mm by the step of 100 mm.

It is seen from FIG. 7 that the spool distortion increases as the distance from the distortion center (the intersection of the axis of the electron lens and the photoelectric cathode 21) increases. Further, the spool distortion increases as the X-ray trajectory distance FID becomes shorter.

Next a correction method for the spool distortion of the conventional X-ray radiograph diagnosis device is described. The X-ray R exposed from the X-ray focus 10 of the X-ray tube 1 falls on the photoelectric cathode 21 of the X-ray image intensifier 2 after transmitting through the object 3. Thus, the photoelectrons E generated from the photoelectric cathode 21 and converged by the electron lens system passes the cross-over point P and irradiates the fluorescent film 26 to form an image of the object 3. The X-ray image generated at the output surface 26*a* of the fluorescent film 26 is digitized by the image processor 4 and the digitized image is displayed on the display device 5.

Under this circumstance, the X-ray tube 1 may be vertically translated as shown in FIG. 5. In accordance with the variation of the X-ray trajectory distance FID, however, the magnitude of the spool distortion integral varies as shown in FIG. 7. Accordingly, the quality of the picture (especially at the periphery of the image) is injured. The diagnosis is thus very difficult. To overcome this difficulty, the voltage applied on the intermediate electrode for correction 25 is adjusted in accordance with the X-ray trajectory distance FID, such that the spool distortion integral remains constant at respective points upon the display screen. However, the spool distortion itself is not eliminated. Further, when the distortion center is not aligned with the axis of the X-ray, an asymmetric spool distortion persists.

Thus, the above conventional X-ray radiograph diagnosis device has the following disadvantage. Since only the voltage applied on the intermediate electrode for correction 25 is controlled, the spool distortion, although kept constant, is not eliminated. Thus, the diagnosis must be performed on the basis of the X-ray image containing the spool distortion. Worse still, when the distortion center is not coaxially aligned with the X-ray center, an asymmetric spool distortion persists. Then, the image is distorted asymmetrically and the spool distortion integral cannot even be kept constant.

SUMMARY OF THE INVENTION

It is therefore an aim of this invention to provide a method for correcting geometric distortions, especially a spool distortion, of an image of the X-ray radiograph diagnosis device, whereby the distortion which is symmetric can be completely eliminated.

The above object is accomplished in accordance with a principle of this invention by a distortion correction method for determining a distortion center of an X-ray image obtained by an X-ray imaging device. The distortion correction method comprises the steps of: (a) preparing a plate-shaped object made of a material and having an X-ray imageable marker pattern therein, the marker pattern including a marker center and at least three sample points positioned at an equal distance from the marker center; (b) positioning the object upon the X-ray imaging device; (c) displaying an X-ray image of the object by means of the X-ray imaging device; and (d) inferring a distortion center of the X-ray imaging device on the basis of displayed distances from the marker center to the sample points.

Alternatively, the distortion correction method for determining a distortion center of an X-ray image comprises the steps of: (a) preparing a plate-shaped object made of a material and having an X-ray imageable marker pattern therein, the marker pattern including a marker center and a plurality of sample points positioned at distinct distances from the marker center upon respective axes of an orthogonal coordinate system; (b) positioning the object upon the X-ray imaging device; (c) displaying an X-ray image of the object by means of the X-ray imaging device; and (d) inferring a distortion center of the X-ray imaging device on the basis of physical and displayed distances from the marker center to the sample points.

Preferably, the distortion correction method further comprises the step of: (e) judging whether or not a difference between the marker center and the inferred distortion center is within a predetermined allowable limit; and (f) repeating steps (b) through (e) until judgment at step (e) is affirmative; and (g) determining as the distortion center inferred at a step (d) immediately preceding the step (e) at which the judgement is affirmative.

Still preferably, the distortion correction method further comprises the steps of: (h) marking a position of the distortion center inferred at step (d) upon the X-ray image intensifier of the X-ray imaging device; and (i) aligning an axis of an exposed X-ray of the X-ray imaging device with the mark.

According to the other aspect of this invention, the distortion correction method for correcting a distortion of an X-ray image comprises the steps of: (a) preparing a plate-shaped object made of a material and having an X-ray imageable marker pattern therein, the marker pattern including a marker center and a plurality of groups of sample points positioned at distinct distances from the marker center; (b) positioning the object upon the X-ray imaging device; (c) displaying an X-ray image of the object by means of the X-ray imaging device; (d) determining physical and displayed distances from the marker center to respective groups of the sample points; (e) determining a relationship between the physical and displayed distances determined at step (d); (f) determining distortion coefficients at respective distances from the distortion center on the basis of the relationship determined at step (e); (g) determining correction coefficients at respective distances from the distortion center on the basis of the distortion coefficients determined at step (f); and (h) correcting the X-ray image on the basis of the correction coefficients determined at step (g).

Preferably, the marker center is positioned substantially at the distortion center. Further, it is preferred that in the step (e) the relationship is approximated by means of a polynomial. Furthermore, in the step (a), the marker pattern is preferred to include a plurality of lattice points arranged in a form of matrix, the groups of sample points consisting of the lattice points.

BRIEF DESCRIPTION OF THE DRAWINGS

The features which are believed to be characteristic of this invention are set forth with particularity in the appended claims. The structure and method of operation of this invention itself, however, will be best understood from the following detailed description, taken in conjunction with the accompanying drawings, in which:

In the drawings, like reference numerals represent like or corresponding parts or portions.

DETAILED DESCRIPTION OF THE PREFERRED EMBODIMENTS

Figure 1:
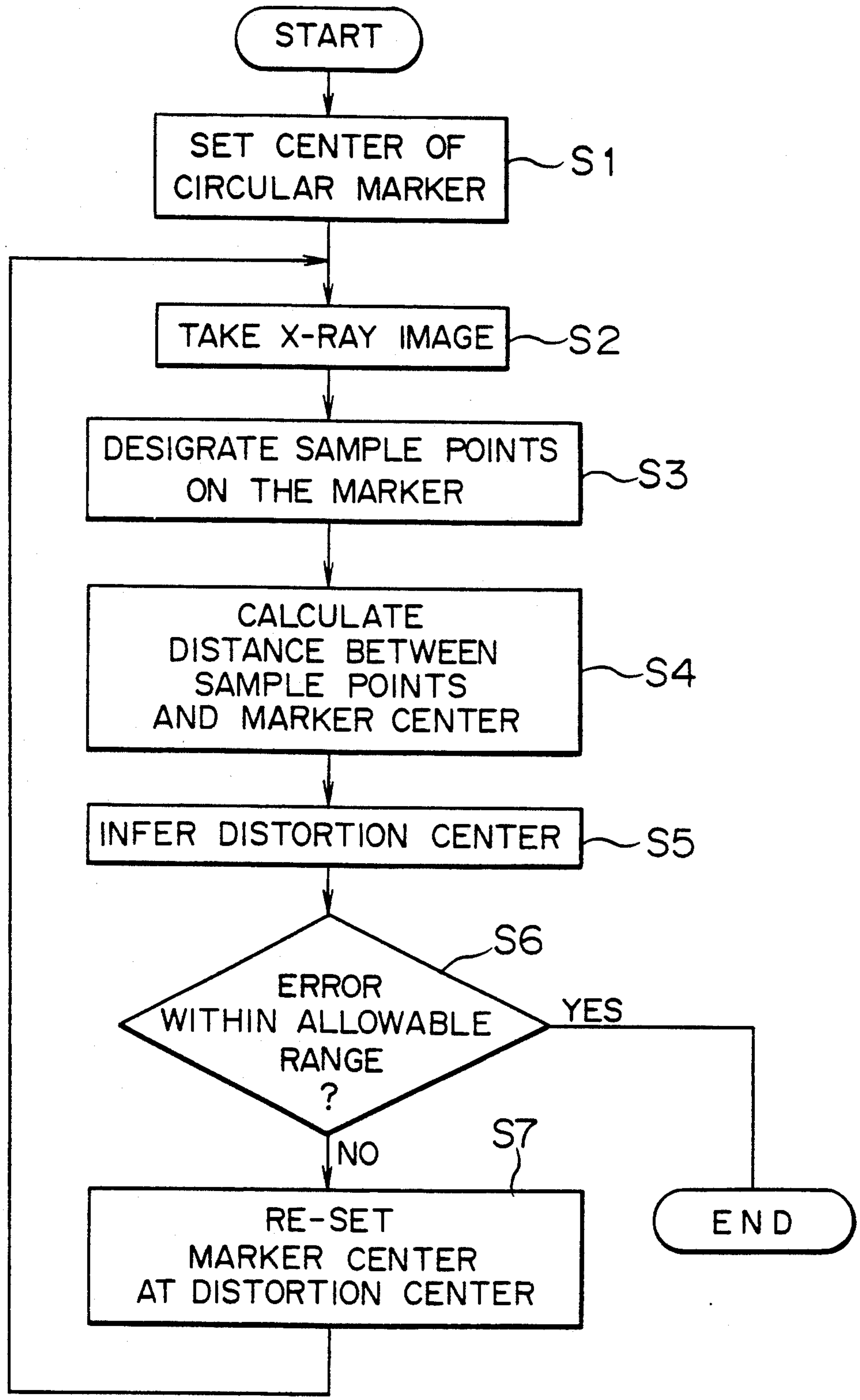
FIG. 1 is a flowchart showing the steps for determining the distortion center by means of a circular marker according to this invention.
Figure 2:
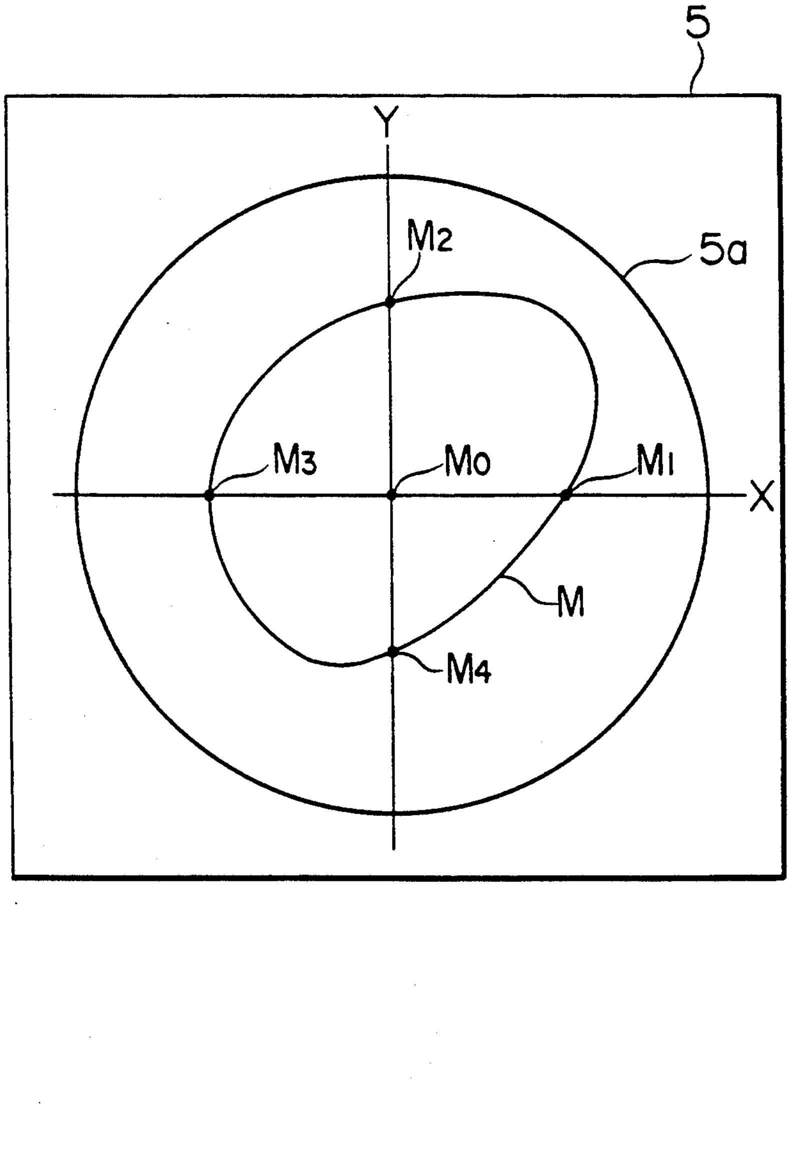
FIG. 2 is a diagram showing the display screen with sample designated points on the circular marker.
Figure 5:
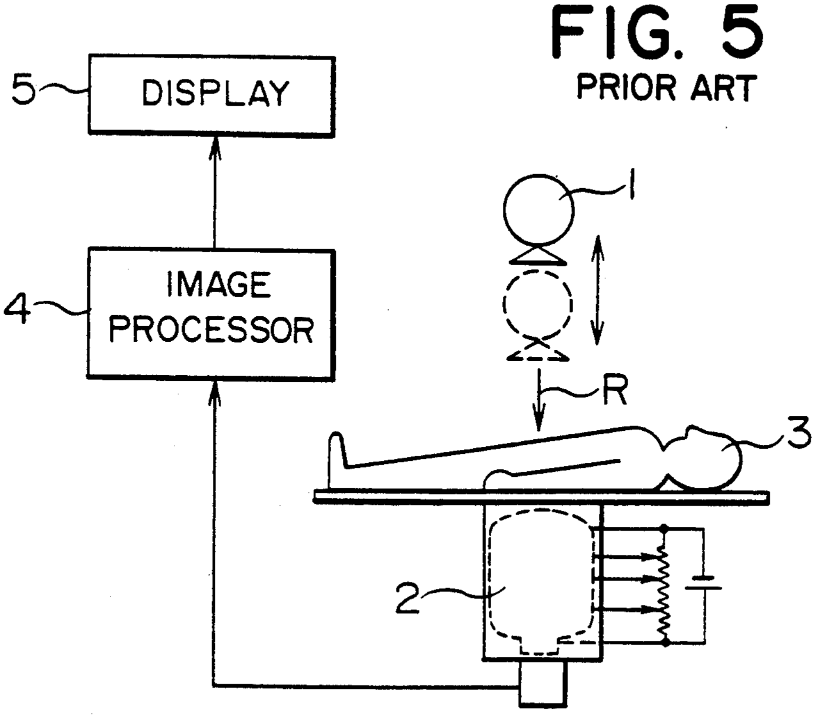
FIG. 5 PRIOR ART
FIG. 5 is a diagram showing the structure of a conventional X-ray radiograph diagnosis device.
Figure 6:
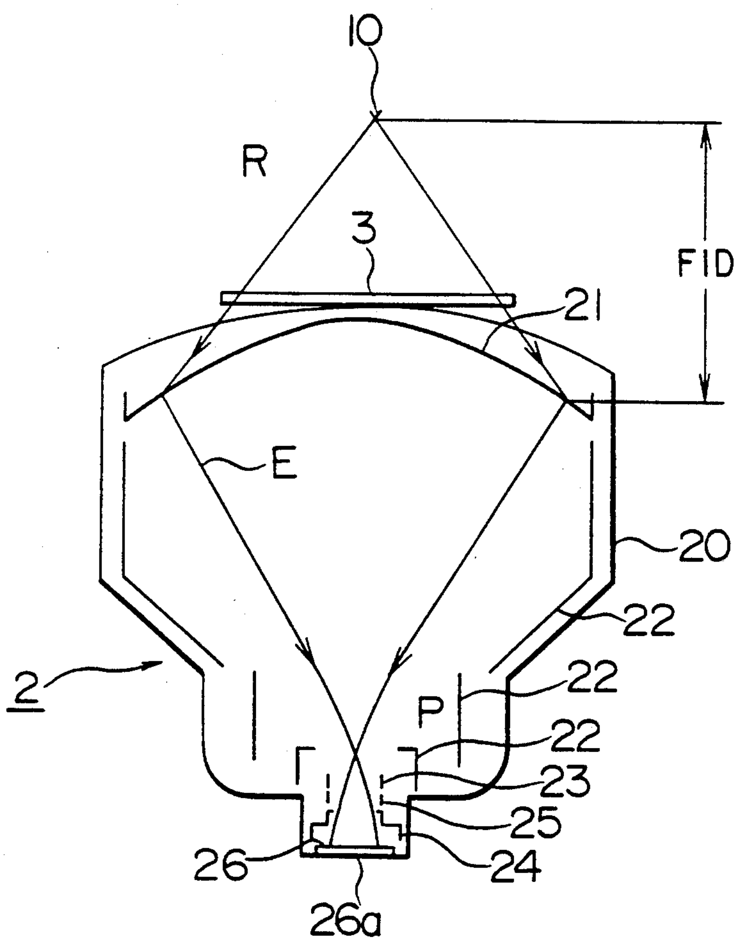
FIG. 6 PRIOR ART
FIG. 6 is an axial sectional view showing the details of the X-ray image intensifier of FIG. 5.
Figure 7:
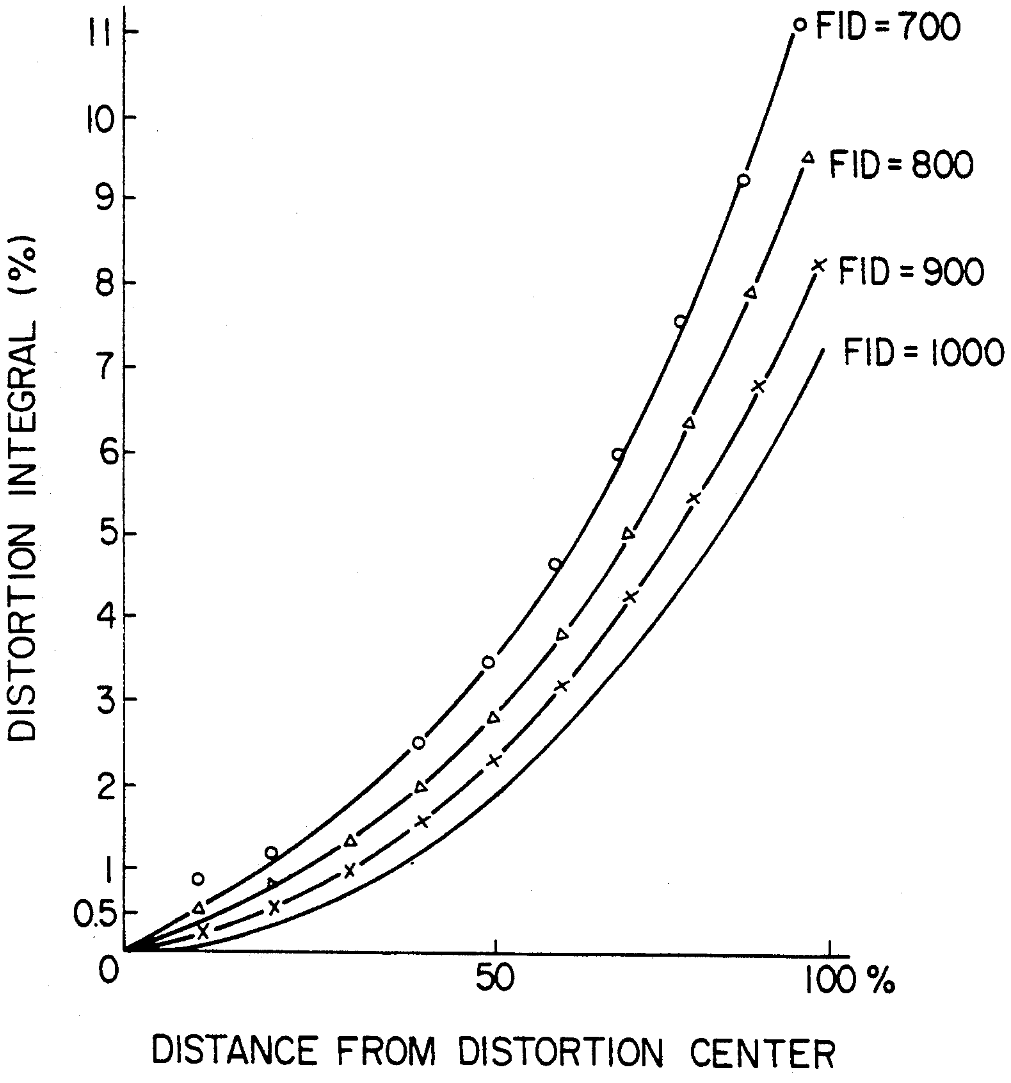
FIG. 7 is a diagram showing the magnitude of the spool distortion (plotted along the ordinate) in relation to distance from the distortion center (plotted along the abscissa) for various values of X-ray trajectory distance FID.

Referring now to the accompanying drawings, the preferred embodiments of this invention are described. FIG. 1 is a flowchart showing the steps for determining the distortion center by means of a circular marker according to this invention. FIG. 2 is a diagram showing the display screen with sample designated points on the circular marker. The distortion center inference (determination) routine of FIG. 1 is implemented as a program, for example, within the image processor 4 or another separate microcomputer processor. The overall structure of the X-ray radiograph diagnosis device is as shown in FIGS. 5 and 6.

As shown in FIG. 2, the display device 5 is provided with a circular cathode ray tube 5*a*, on which a circular marker M with a marker center $M_0$ is displayed. The four sample points $M_1$ through $M_4$ are determined as the intersections of the circular marker M and the orthogonal coordinate axes X-Y the origin of which coincides with the marker center $M_0$ of the circular marker M.

Next, referring to FIGS. 1 and 2 and FIGS. 5 through 7, the method for determining the distortion center by means of the circular marker M is described.

First, a plate-shaped object 3, made of a material is not entirely transparent the X-ray, is prepared, wherein the circular marker M (a circular pattern) and the marker center $M_0$ (a central point) are formed through the object 3. Then, at step S1 in FIG. 1, the object 3 having the circular marker M with the marker center $M_0$ is positioned on the front surface of the X-ray image intensifier 2 such that the marker center $M_0$ is in registry with the centeral axis of the X-ray tube 1 and the X-ray image intensifier 2.

Next, at step S2, the X-ray R generated by the X-ray tube 1 is irradiated on the object 3, and the X-ray image of the circular marker M is formed on the fluorescent film 26 within the X-ray image intensifier 2. The X-ray image is digitized by the image processor 4 and is immediately displayed on the display device 5 as shown in FIG. 2. If the distortion center coincides with the marker center $M_0$, the circular marker M is displayed as a true circle on the circular cathode ray tube 5a. However, the distortion center generally does not coincide with the marker center $M_0$, and the image of the circular marker M upon the display device 5 is thus distorted as shown in FIG. 2.

At step S3, four sample points $M_1$ through $M_4$, for example, are designated on the circular marker M displayed on the circular cathode ray tube 5a of the display device 5. The marker center $M_0$ is displayed and designated automatically.

Next, at step S4, the distances between the marker center $M_0$ and the respective sample points $M_1$ through $M_4$ as displayed on the screen on the circular cathode ray tube 5a are calculated. As noted above, the magnitude of the spool distortion is approximately a function of, and hence is determined by, the distance from the distortion center. Thus, the sample points that are farther away from the distortion center are displayed at greater distances from the marker center $M_0$. Thus, when the marker center $M_0$ does not coincide with the distortion center, the distances from the marker center $M_0$ to the sample points $M_1$ through $M_4$ are differentiated. On the other hand, when the marker center $M_0$ coincides with the distortion center, the circular marker M becomes a true circle with the marker center $M_0$ positioned at the center thereof. Under this circumstance, the distances from the marker center $M_0$ to the sample points $M_1$ through $M_4$ are equal.

Thus, at step S5, the distortion center is inferred (calculated) by the image processor 4, for example, as follows. First, the middle points of the respective two sample points lying on the same axis (the X- or Y-axis), namely, the middle point of $M_1$ and $M_3$ lying on the X-axis and the middle point of $M_2$ and $M_4$ lying on the Y-axis, are determined. Then, the middle point of the these two middle points is determined. The last middle point is inferred to be the distortion center upon the circular cathode ray tube 5a of the display device 5.

Next, on the basis of the distances from the marker center $M_0$ to the respective sample points $M_1$ through $M_4$ on the display screen and the real or physical radius of the circular marker M upon the object 3 which is known beforehand, the position upon the photoelectric cathode 21 of the X-ray image intensifier 2 which corresponds to the position of the distortion center inferred upon the circular cathode ray tube 5a as described above is calculated.

Then at step S6, the real position of the marker center $M_0$ upon the photoelectric cathode 21 is compared with the inferred position of the distortion center upon the photoelectric cathode 21, and it is determined whether or not the error (the physical distance between the real marker center $M_0$ and the inferred distortion center) is within a predetermined allowable range. As noted above, the marker center $M_0$ is displayed at an equal distance from the sample points $M_1$ through $M_4$ when the marker center $M_0$ coincides with the distortion center. Thus, the error or the distance between the marker center $M_0$ and the inferred distortion center vanished when the marker center $M_0$ is accurately positioned at the distortion center. If the error is larger than the predetermined range (that is, if the real or physical position of the marker center $M_0$ is displaced from the inferred distortion center beyond the predetermined limit), the reliability of the position of the distortion center inferred at the preceding step S5 is deemed low.

Thus, when the judgment at step S6 is negative at step S6, the object 3 having the circular marker M is translated upon the photoelectric cathode 21 and the marker center $M_0$ is re-positioned at step S7 such that the marker center $M_0$ coincides with the distortion center inferred at the preceding step S5. Thereafter, the steps S2 through S6 are repeated until the error is within the predetermined allowable limit at step S6.

When the error or the distance between the marker center $M_0$ and the distortion center is finally judged to be within the allowable limit at step S6, the inferred distortion center is determined as the distortion center. The position of the distortion center upon the photoelectric cathode 21 thus finally determined at step S6 is marked, and the distortion center inference or determination routine of FIG. 1 is terminated.

When an object 3 such as a human body is diagnosed, the axes of the X-ray tube 1 and the X-ray image intensifier 2 can be adjusted to the (inferred) distortion center with the mark upon the photoelectric cathode 21 as the target. Further, the position of the distortion center upon the circular cathode ray tube 5a may be stored in the image processor 4.

Since the distortion center is determined precisely as described above, the correction of the spool distortion by means of the intermediate electrode for correction 25, for example, can be effected symmetrically. The reliability of distortion correction is thus unchanged or unaffected. The displayed image contains only a symmetric spool distortion and the asymmetric distortion is eliminated.

By the way, in the case of the above embodiment, the middle point of the two middle points of respective two sample points lying on the same axes is inferred as the distortion center. However, the distortion center may be inferred as follows: (1) First, the ratio of the distances from the marker center $M_0$ to the two sample points on the same axis is determined with respect to the respective axes X and Y. (2) Second, the point on the respective axes whose distances from the two sample points are inversely proportional to the ratio of the distances as determined at step (1) is determined as the inferred distortion center along the respective axes. (3) Finally, the point having the X- and Y-coordinate equal to those of the distortion centers along the X- and Y-axes, respectively, that are inferred at step (2) is inferred as the distortion center in the X-Y plane.

For example, let it be assumed that at step (1), the ratio of the distances from the marker center $M_0$ to $M_1$ and $M_3$ lying on the X-axis is 2: 1. Then, at step (2), the point $M_5$ (not shown) on the X-axis whose distance from the sample points $M_1$ and $M_3$ are 1: 2 (inversely proportional to the above ratio 2: 1) is inferred as the distortion center along the X-axis. The distortion center $M_6$ (not shown) on the Y-axis is determined in a similar manner. Then, at step (3), the point $M_7$ (not shown) having the X-coordinate equal to that of the point $M_5$ and the Y-coordinate equal to that of the point $M_6$ is inferred as the distortion center in the X-Y plane.

Alternatively, the distortion center may be inferred by the method of least squares. Then, a point or position P is determined within the X-Y plane such that a variance of the distances from the position P to the four sample points $M_1$ through $M_4$ is at the minimum. The position thus determined is inferred to be the distortion center. Still alternatively, the position may be inferred by the symlex method such that the variance of the distances from the position to the four sample points $M_1$ through $M_4$ is at the minimum.

Further, the number of sample points designated on the circular marker M is not limited to four; it may be three or more than four. Furthermore, in the case of the above embodiment, the distances from the marker center $M_0$ to the sample points upon the X-ray image display are used for the inference of the distortion center. However, the numbers of pixels upon the circular cathode ray tube 5a may be used for calculating the distances. Still further, the distortion center may be determined by the operator by means of the trial and error method, by seeking a suitable position at which the circular marker M becomes a true circle upon the circular cathode ray tube 5a.

Figure 3:
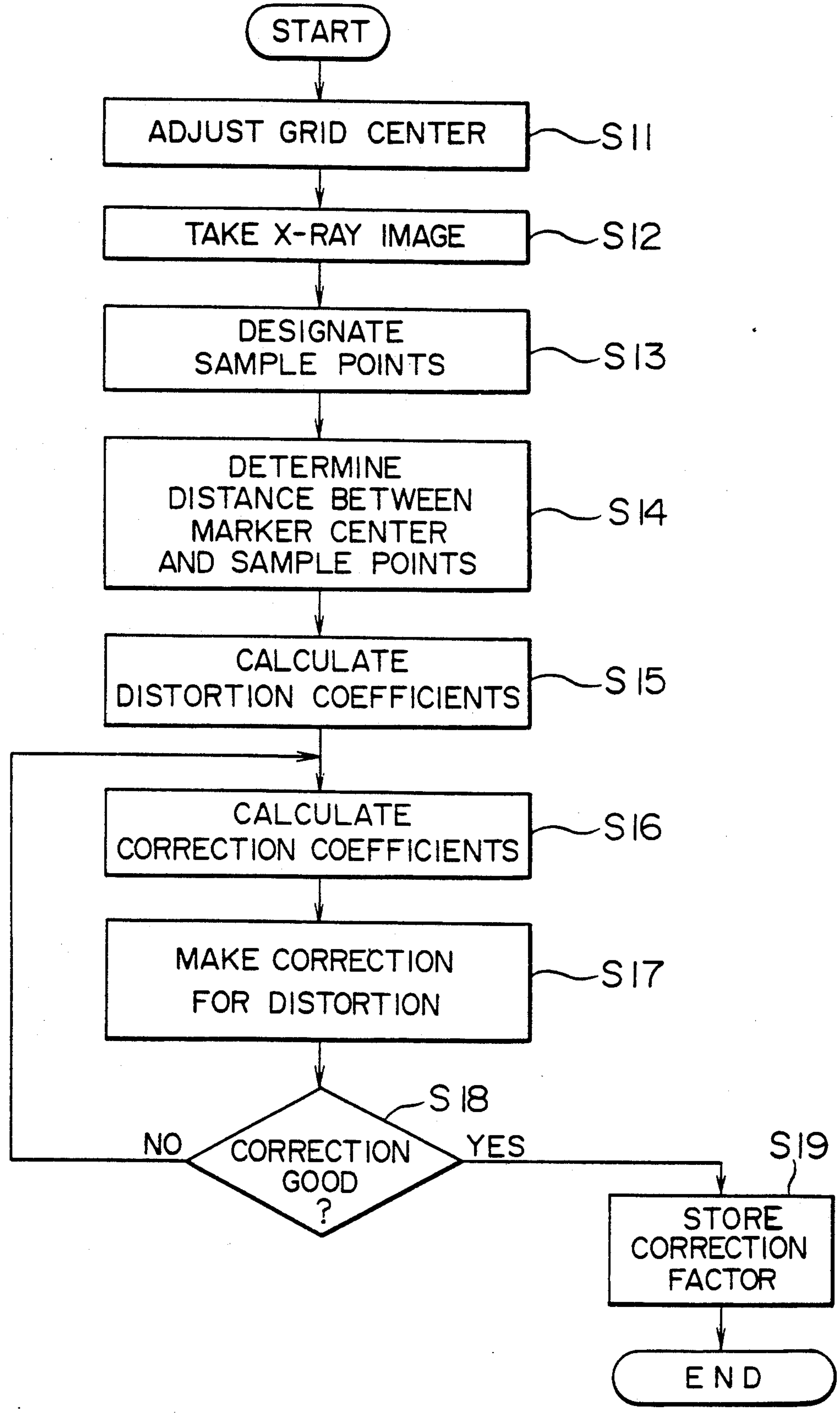
FIG. 3 is a flowchart showing the steps for determining the spool distortion correction coefficients by means of a grid marker according to this invention.

FIG. 3 is a flowchart showing the steps for determining the spool distortion correction coefficients by means of a grid marker according to this invention. According to this method, a grid marker is used instead of the circular marker. As described below, the correction coefficients for the spool distortion corresponding to the image position can be determined by calculation.

Figure 4:
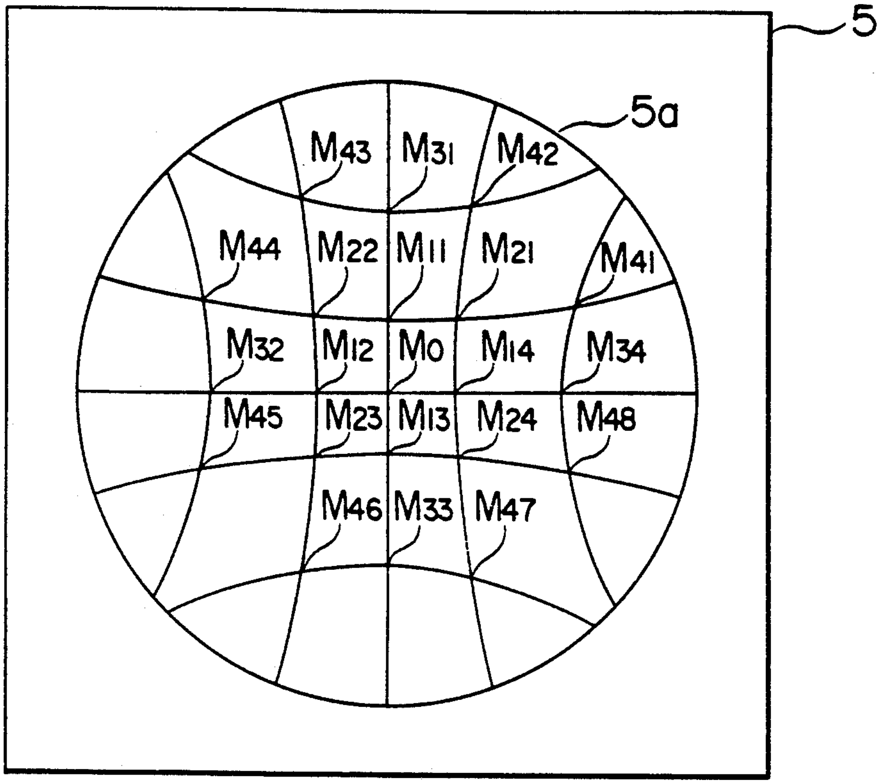
FIG. 4 is a diagram showing the display screen with sample points on the grid marker.

FIG. 4 is a diagram showing the display screen with sample points on the grid marker. Marker center $M_0$ is the lattice point at the center of the grid marker. The orthogonal grid lines meeting at marker center $M_0$ correspond to the orthogonal coordinate axes X and Y, respectively. Thus, the rotational display position of the orthogonal coordinate system is determined by the grid marker. Further, the lattice points $M_{11}$ through $M_{48}$ at the intersections of the respective grid marker lines are arranged at equal distances from each other in the form of a matrix on the physical grid marker formed on the object 3. Due to the spool distortion, however, the distances among the lattice points $M_{11}$ through $M_{48}$ are displayed differentiated upon the circular cathode ray tube 5a of the display device 5.

Next the method of determining the spool distortion correction coefficients is described by referring to FIGS. 3 through 7. It is assumed that the distortion center is already determined by means of the routine of FIG. 1 as described above, and the position of the determined distortion center is marked on the photoelectric cathode 21. Further, it is assumed that the central axis of the X-ray is adjusted to the distortion center.

First a plate-shaped object 3, made of a material which is not transparent to the X-ray is prepared. The grid marker, consisting of two systems of equally spaced parallel grid lines and meeting at right angles with each other, is formed through the object 3. At step S11, this object 3 is positioned on the X-ray image intensifier 2 such that the marker center $M_0$ is substantially at the axis of the X-ray tube 1 and the X-ray image intensifier 2 and the marker center $M_0$ is at or near the distortion center. It is not required that the marker center $M_0$ be precisely at the distortion center.

Next, at step S12, the X-ray R generated from the X-ray tube 1 is irradiated on the object 3, and the X-ray image of the grid marker is formed on the fluorescent film 26 of the X-ray image multiplier 2. The X-ray image is digitized by the image processor 4 and then is displayed on the display device 5 as shown in FIG. 4. The marker center $M_0$ is positioned substantially at the distortion center. Thus, as shown in FIG. 4, the spool distortion is substantially symmetric with respect to the marker center $M_0$.

Next, at step S13, the marker center $M_0$ is designated upon the grid marker displayed on the circular cathode ray tube 5a of the display device 5. Further, the groups of the lattice points separated from the marker center $M_0$ by equal distances (for example, the group of $M_{11}$ through $M_{14}$, the group of $M_{21}$ through $M_{24}$, the group of $M_{31}$ through $M_{34}$, and the group of $M_{41}$ through $M_{48}$) are designated as groups of sample points at equal distances.

At step S14, the distances from the marker center $M_0$ to the respective sample points $M_{11}$ through $M_{48}$ are determined on the basis of, for example, the numbers of the pixels corresponding to the respective points upon the circular cathode ray tube 5a.

The real or physical distances from the marker center $M_0$ to the respective sample points $M_{11}$ through $M_{48}$ upon the object 3 are known beforehand. Further, the degree of the spool distortion is substantially a function of the distance from the distortion center. Thus, a group of sample points at an equal (physical) distance from the marker center $M_0$ upon the object 3 (for example, the sample points $M_{21}$ through $M_{24}$) are also substantially at a equal distance from the marker center $M_0$ upon the display.

Thus, at step S15, on the basis of the distances from the marker center $M_0$ to the respective sample points $M_{11}$ through $M_{48}$ upon the circular cathode ray tube 5a and the real or physical distances from the marker center $M_0$ to the respective sample points $M_{11}$ through $M_{48}$ upon the object 3 having the grid marker, the distortion coefficients representing the magnitudes of the spool distortion at the respective sample points are determined. The method of determination of the distortion coefficients is described in detail below.

Next, at step S16, on the basis of the reciprocal numbers of the distortion coefficients calculated at step S15, the spool distortion correction coefficients for adjusting the displayed positions of the marker center $M_0$ and the respective sample points $M_{11}$ through $M_{48}$ such that they coincide with the respective real positions thereof upon the 3 are calculated. The method to determine correction coefficients is described in detail below. At step S17, the X-ray image of the grid marker is corrected by the image processor 4, for example, on the basis of the spool distortion correction coefficients determined at the preceding step S16.

At step S18, by displaying the image of the grid marker upon the circular cathode ray tube 5a, the operator judges whether or not the corrected image is sufficiently good (that is, whether or not the displayed image is a sufficiently faithful representation of the grid marker upon the object 3). If the judgment is negative, the control returns to step S16, and the spool distortion correction coefficients are re-calculated and the distortion is corrected accordingly, until the image of the grid marker is substantially faithfully reproduced upon the circular cathode ray tube 5a.

When it is finally confirmed at step S18 that the corrected X-ray image of the grid marker displayed on the circular cathode ray tube 5a is good enough, the spool distortion correction coefficients obtained at the final correction at step S16 are stored as the spool distortion correction coefficients data. When the imaged body 3 consists of a human body thereafter, the X-ray display image is corrected systematically, for example, by the image processor 4. Thus, highly precise X-ray image is obtained, such that the reliability of the diagnosis is improved.

In the above procedure, the spool distortion correction coefficients can be calculated as follows. The real or physical distances from the marker center $M_0$ to the respective sample points upon the plate-shaped object 3 are plotted along the abscissa X. The corresponding distances upon the circular cathode ray tube 5*a* are plotted along the ordinate Y. The points having X- and Y-coordinates equal to the physical and displayed distances of respective sample points are plotted on the X-Y plane. These points represent the relationship or correspondance between the physical distance (plotted along the X-axis) and the displayed distance (plotted along the Y-axis). Then the relationship between the physical and the displayed distances are fitted by means of a polylnomial curve. Thus, the power factor and the coefficients of the polynomial curve substantially connecting the plotted points is determined, by, for example, the method of least squares.

The correction coefficient is a function of the displayed distance y. This correction coefficient function is an inverse function of the function determined by the above polynomial curve in the X-Y plane. If the correction function is represented by: $x=f(y)$, the function for the polynomial curve connecting the points plotted on the X-Y plane as described above is represented by: $y=f^{-1}(x)$, where $f^{-1}(x)$ represents the inverse function of f(y). When the marker center $M_0$ coincides with the distortion center, the polynomial function for the plotted points is represented by: $y=a\ x^n$, since the spool distortion is symmetric with respect to the marker center $M_0$. Then, the correction function is represented by: $x=(y/a)^{-n}$. Under this condition, the spool distortion is determined by the N-th power polynomial passing the origin of the X-Y plane. The values of the n and the coefficient a are determined from among those for the curves passing the respective sample points. The determination is made, for example, by means of the method of least squares.

When, on the other hand, the marker center $M_0$ is displaced from the distortion center at the initial step S11, the function of the curve connecting the plotted points is represented by the polynomial: $y=a_n x^n+a_{n-1} x^{n-1}+ \cdots + a_1 x+a_0$, where the coefficients $a_0$ through $a_n$ are determined likewise by the method of least squares. It goes without saying that the power factor n of the polynomial is less than the number of the distinct groups of the sample points at equal distances from the marker center $M_0$. (In the case shown in FIG. 4, the number is four: there are four groups consisting respectively of sample points $M_{11}$ through $M_{14}$, $M_{21}$ through $M_{24}$, $M_{31}$ through $M_{34}$, and $M_{41}$ through $M_{48}$.) Alternatively, the polynomial may be determined by means of the symplex method instead of the method of least squares.

Further, the distances from the marker center $M_0$ to the respective sample points $M_{11}$ through $M_{48}$ as displayed on the circular cathode ray tube 5*a* may be used, instead of the number of pixels. Further, although the above embodiment uses a grid marker, any type of markers may be used provided that the distances from the marker center $M_0$ to the sample points are known. For example, the intersections of a plurality of circular markers with the orthogonal coordinate axes may be used as the sample points.

Furthermore, in the above embodiment, the description is made of the case where the distortion center is determined beforehand, and the marker center $M_0$ is adjusted to the distortion center at step S11. However, even if the distortion center is not inferred beforehand, the distortion center can be inferred using the grid marker.

Namely, as shown in FIG. 4, take the orthogonal coordinate system X-Y having the marker center $M_0$ as the origin upon the screen. Then, the distances from the marker center $M_0$ to the respective sample points on the X-axis: $M_{12}$, $M_{14}$, $M_{32}$, and $M_{34}$, and the distances from the marker center $M_0$ to the respective sample points on the Y-axis: $M_{11}$, $M_{13}$, $M_{31}$, and $M_{33}$, are determined.

Next, the relationship between the actual or physical distance upon the object 3 and the distance upon the display screen for the respective sample points upon the X-axis ($M_{12}$, $M_{14}$, $M_{32}$, and $M_{34}$) is approximated by a polynomial: $q=g(p)=b_n p_n+b_{n-1} p^{n-1} + \cdots b_1 p+b_0$. The respective coefficients $b_0$ through $b_n$ of the polynomial are determined, for example, by the method of least squares or the symplex method. The polynomial for the sample points on the Y-axis is determined in a similar manner.

Next, the coordinate value $p_0$ for adjusting the marker center $M_0$ to the distortion center is calculated by determining, by means of the method of least squares or the symplex method, the value $p_0$ satisfying the N-th power function $q=g(p)=b_n (p-p_0)^n$.

If the value of $p_0$ determined for the X- and Y-axes are represented by: $X_0$ and $Y_0$, respectively, the coordinates of the distortion center: $(X_0, Y_0)$ can be inferred. Then the marker center $M_0$ can be adjusted to the inferred distortion center. Thus, in a similar manner to that above, the correction coefficients for the respective lattice points can be determined on the basis of the inferred distortion center.

What is claimed is:

1. A distortion correction method for determining a distortion center of an X-ray image obtain by an X-ray imaging device, said distortion correction method comprising the steps of:

(a) preparing a plate-shaped object having an X-ray imageable marker pattern therein, said marker pattern including a marker center and at least three sample points positioned at an equal distance from said marker center;

(b) positioning said object upon said X-ray imaging device;

(c) displaying an X-ray image of said object by means of said X-ray imaging device; and (d) inferring a distortion center of said X-ray imaging device on the basis of displayed distances from said marker center of said sample points.

2. A distortion correction method as claimed in claim 1, wherein said distortion is a spool distortion of said X-ray imaging device.

3. A distortion correction method for determining a distortion center of an X-ray image obtained by an X-ray imaging device, said distortion correction method comprising the steps of:

(a) preparing a plate-shaped object having an x-ray imageable marker pattern therein, said marker pattern including a marker center and a plurality of sample points position at distinct distance from said marker center upon respective axes of an orthogonal coordinate system;

(b) positioning said object upon said X-ray imaging device;

(c) displaying an X-ray image of said object by means of said X-ray imaging device; and (d) inferring a distortion center of said X-ray imaging device on the basis of displayed distances from said marker center of said sample points.

4. A distortion correction method as claimed in claim 3, wherein said distortion is a spool distortion of said X-ray imaging device.

5. A distortion correction method as claimed in claim 1, further comprising the step of:

(e) judging whether or not a difference between said marker center and said inferred distortion center is within a predetermined allowable limit; and (f) repeating said steps (b) through (e) until judgment at step (e) is affirmative; and (g) determining as a distortion center inferred at said step (d) preceding step (e) at which said judgement is affirmative.

6. A distortion correction method as claimed in claim 3, further comprising the step of:

(e) judging whether or not a difference between said marker center and said inferred distortion center is within a predetermined allowable limit; and (f) repeating steps (b) through (e) until judgment at step (e) is affirmative; and (g) determining as a distortion center inferred at said step (d) preceding step (e) at which said judgement is affirmative.

7. A distortion correction method as claimed in claim 1, wherein said X-ray imaging device comprises an X-ray image intensifier upon which the imaged body is positioned, said distortion correction method further comprising the steps of:

(h) marking a position of said distortion center inferred at step (d) upon said X-ray image intensifier of said X-ray imaging device; and (i) aligning an axis of an imaging X-ray of said X-ray imaging device with said mark upon said X-ray image multiplier.

8. A distortion correction method as claimed in claim 3, wherein said X-ray imaging device comprises an X-ray image intensifier upon which the imaged body is positioned, said distortion correction method further comprising the steps of:

(h) marking a position of said distortion center inferred at step (d) upon said X-ray image intensifier of said X-ray imaging device; and (i) aligning an axis of an imaging X-ray of said X-ray imaging device with said mark upon said X-ray image intensifier.

9. A distortion correction method for correcting a distortion of an X-ray image obtained by an X-ray imaging device, wherein a distortion center of said X-ray image is determined beforehand, said distortion correction method comprising the steps of:

(a) preparing a plate-shaped object having an x-ray imageable marker pattern therein, said marker pattern including a marker center and a plurality of groups of sample points positioned at distinct distances from said marker center upon respective axes of an orthogonal coordinate system;

(b) positioning said object upon said X-ray imaging device;

(c) displaying an X-ray image of said object by means of said X-ray imaging device;

(d) determining physical and displayed distances from said marker center to respective groups of said sample points;

(e) determining a relationship between said physical and displayed distances determined at step (d);

(f) determining distortion coefficients at respective distances from said distortion center on the basis of said relationship determined at step (e);

(g) determining correction coefficients at respective distances from said distortion center on the basis of said distortion coefficients determined at step (f); and (h) correcting said X-ray image on the basis of said correction coefficients determined at step (g).

10. A distortion correction method as claimed in claim 9, wherein in said step (b), said marker center is positioned substantially at said distortion center.

11. A distortion correction method as claimed in claim 9 wherein in said step (e) said relationship is approximated by means of a polynomial.

12. A distortion correction method as claimed in claim 9, wherein in said step (a), said marker pattern includes a plurality of lattice points arranged in a form of matrix, said groups of sample points consisting of said lattice points.

13. A distortion correction method as claimed in claim 9, wherein said X-ray imaging device includes a digital display device, said X-ray image being displayed on said display device in said step (c); and said distances from said marker center to said sample points are determined on the basis of number of pixels between respective points on said display device.

* * * * *

UNITED STATES PATENT AND TRADEMARK OFFICE

CERTIFICATE OF CORRECTION

PATENT NO. : 5,263,074

DATED : November 16, 1993

INVENTOR(S) : Hidenobu Sakamoto

It is certified that error appears in the above-indentified patent and that said Letters Patent is hereby corrected as shown below:

On title page,"Abstract" line 9, "pincushion" should read --spool-- Col. 1, line 13, "imaged" should be -- image --; Col. 4, line 51, after "material" but before "is", insert -- which --; Col. 5, line 35, delete "the", second occurrence; Col. 8, line 37, after "the", first occurrence, but before "3", insert -- object --.

Signed and Sealed this

Third Day of May, 1994

Attest:

Bruce Lehman

BRUCE LEHMAN

*Attesting Officer* *Commissioner of Patents and Trademarks*